(12) United States Patent
Nishide

(10) Patent No.: US 11,869,183 B2
(45) Date of Patent: Jan. 9, 2024

(54) ENDOSCOPE PROCESSOR, INFORMATION PROCESSING DEVICE, AND ENDOSCOPE SYSTEM

(71) Applicant: HOYA CORPORATION, Tokyo (JP)

(72) Inventor: Akihiko Nishide, Tokyo (JP)

(73) Assignee: HOYA CORPORATION, Tokyo (JP)

( * ) Notice: Subject to any disclaimer, the term of this patent is extended or adjusted under 35 U.S.C. 154(b) by 413 days.

(21) Appl. No.: 17/279,893

(22) PCT Filed: Aug. 30, 2019

(86) PCT No.: PCT/JP2019/034230
§ 371 (c)(1),
(2) Date: Mar. 25, 2021

(87) PCT Pub. No.: WO2020/194785
PCT Pub. Date: Oct. 1, 2020

(65) Prior Publication Data
US 2021/0398274 A1    Dec. 23, 2021

(30) Foreign Application Priority Data
Mar. 28, 2019 (WO) .................. PCT/JP2019/013739

(51) Int. Cl.
*G06T 7/00* (2017.01)
*G06T 5/00* (2006.01)
*H04N 25/60* (2023.01)

(52) U.S. Cl.
CPC ............ *G06T 7/0012* (2013.01); *G06T 5/002* (2013.01); *G06T 5/006* (2013.01); *H04N 25/60* (2023.01);
(Continued)

(58) Field of Classification Search
CPC ....... G06T 7/0012; G06T 5/002; G06T 5/006; G06T 2207/10068; G06T 2207/20081;
(Continued)

(56) References Cited

U.S. PATENT DOCUMENTS

2009/0073257 A1    3/2009  Tanaka et al.
2014/0085686 A1    3/2014  Ishihara
(Continued)

FOREIGN PATENT DOCUMENTS

CN    103547207    1/2014
JP    2002-165757   6/2002
(Continued)

OTHER PUBLICATIONS

Official Communication issued in International Bureau of WIPO Patent Application No. PCT/JP2019/034230, dated Nov. 12, 2019, along with an English translation thereof.
(Continued)

*Primary Examiner* — Oschta I Montoya
(74) *Attorney, Agent, or Firm* — GREENBLUM & BERNSTEIN, P.L.C.

(57) ABSTRACT

An endoscope processor according to one aspect includes an image acquisition unit that acquires a captured image from an endoscope, a first correction unit that corrects the captured image acquired by the image acquisition unit, a second correction unit that corrects the captured image acquired by the image acquisition unit, and an output unit that outputs an endoscopic image based on the captured image corrected by the first correction unit and a recognition result using a trained image recognition model in which the recognition result is output in a case where the captured image corrected by the second correction unit is input.

10 Claims, 13 Drawing Sheets

(52) U.S. Cl.
CPC .............. *G06T 2207/10068* (2013.01); *G06T 2207/20081* (2013.01)

(58) Field of Classification Search
CPC . G06T 2207/10016; G06T 2207/10024; G06T 2207/20076; G06T 2207/30092; G06T 1/00; G06T 7/70; H04N 25/60; A61B 1/045
See application file for complete search history.

(56) References Cited

U.S. PATENT DOCUMENTS

2014/0355826 A1* 12/2014 Mitsui .................. G06V 10/811
382/106
2018/0333045 A1* 11/2018 Yamanashi ...... A61B 1/000094
2019/0374141 A1* 12/2019 Yamamoto ........... A61B 1/0638

FOREIGN PATENT DOCUMENTS

| JP | 2006-227774 | 8/2006 |
| JP | 2010-220794 | 10/2010 |
| JP | 2014-232470 | 12/2014 |
| WO | 2008/044365 | 4/2008 |
| WO | 2012/165505 | 12/2012 |
| WO | 2018/155560 | 8/2018 |

OTHER PUBLICATIONS

May 31, 2023 Chinese Office Action in corresponding Chinese Application No. 201980064356.2.

* cited by examiner

OBJECT  CAPTURED IMAGE  AFTER GEOMETRIC CORRECTION

AFTER CORRECTION, ACQUISITION OF REFERENCE RECTANGULAR REGION

EXPLANATION DIAGRAM ILLUSTRATING EXAMPLE OF RECORD LAYOUT OF CORRECTION DB

| MANAGEMENT ID | CORRECTION TYPE | CORRECTION DATA |
|---|---|---|
| 0001 | OFFSET CORRECTION | ****** |
| 0002 | GAMMA CORRECTION | ****** |
| 0003 | WHITE BALANCE CORRECTION | ****** |
| 0004 | GAIN CORRECTION | ****** |
| 0005 | SHADING CORRECTION | ****** |

~271

ENDOSCOPE PROCESSOR, INFORMATION PROCESSING DEVICE, AND ENDOSCOPE SYSTEM

TECHNICAL FIELD

The present invention relates to an endoscope processor, an information processing device, an endoscope system, a program, and an information processing method.

BACKGROUND ART

In recent years, there are various image processing techniques for improving the detection accuracy in endoscopic examination. For example, Patent Literature 1 discloses a detection device that accurately detects a target region from an image by performing a detection process based on distance information using a learning feature amount that reflects a distance.

CITATION LIST

Patent Literature

Patent Literature 1: JP 2014-232470 A

SUMMARY OF INVENTION

Technical Problem

However, in the invention of Patent Literature 1, a feature amount is extracted from an endoscopic image suitable for observation by a doctor. Therefore, there is a concern that the feature amount of the image may be not accurately obtained due to the geometric distortion of the image, the lack of uniformity of all pixels, and the like, and the target region may not be extracted correctly.

In one aspect, it is an object of the present invention to provide an endoscope processor and the like capable of outputting an accurate recognition result in an image recognition process using a trained image recognition model.

Solution to Problem

An endoscope processor according to one aspect includes an image acquisition unit that acquires a captured image from an endoscope, a first correction unit that corrects the captured image acquired by the image acquisition unit, a second correction unit that corrects the captured image acquired by the image acquisition unit, and an output unit that outputs an endoscopic image based on the captured image corrected by the first correction unit and a recognition result using a trained image recognition model in which the recognition result is output in a case where the captured image corrected by the second correction unit is input.

Advantageous Effects of Invention

On one aspect, it is possible to output an accurate recognition result in an image recognition process using a trained image recognition model.

DESCRIPTION OF EMBODIMENTS

Hereinafter, the present invention will be described in detail with reference to the drawings illustrating the embodiments thereof.

First Embodiment

The first embodiment relates to a mode in which an image (captured image) captured from an endoscope is subjected to a correction process and then to an image recognition process. The endoscope includes a flexible endoscope or rigid endoscope. The flexible endoscope is a fiberscope that guides the image captured by the lens system at the tip to the eyepiece outside the body with a glass fiber and observes it with the naked eye, and an endoscope that captures an image by charge coupled device (CCD), charge modulation device (CMD), or complementary metal oxide semiconductor (CMOS) at the tip and electrically guides it to a monitor for observation. A rigid endoscope is an endoscope in which a lens system is connected from the tip for observation at an eyepiece outside the body.

Figure 1:
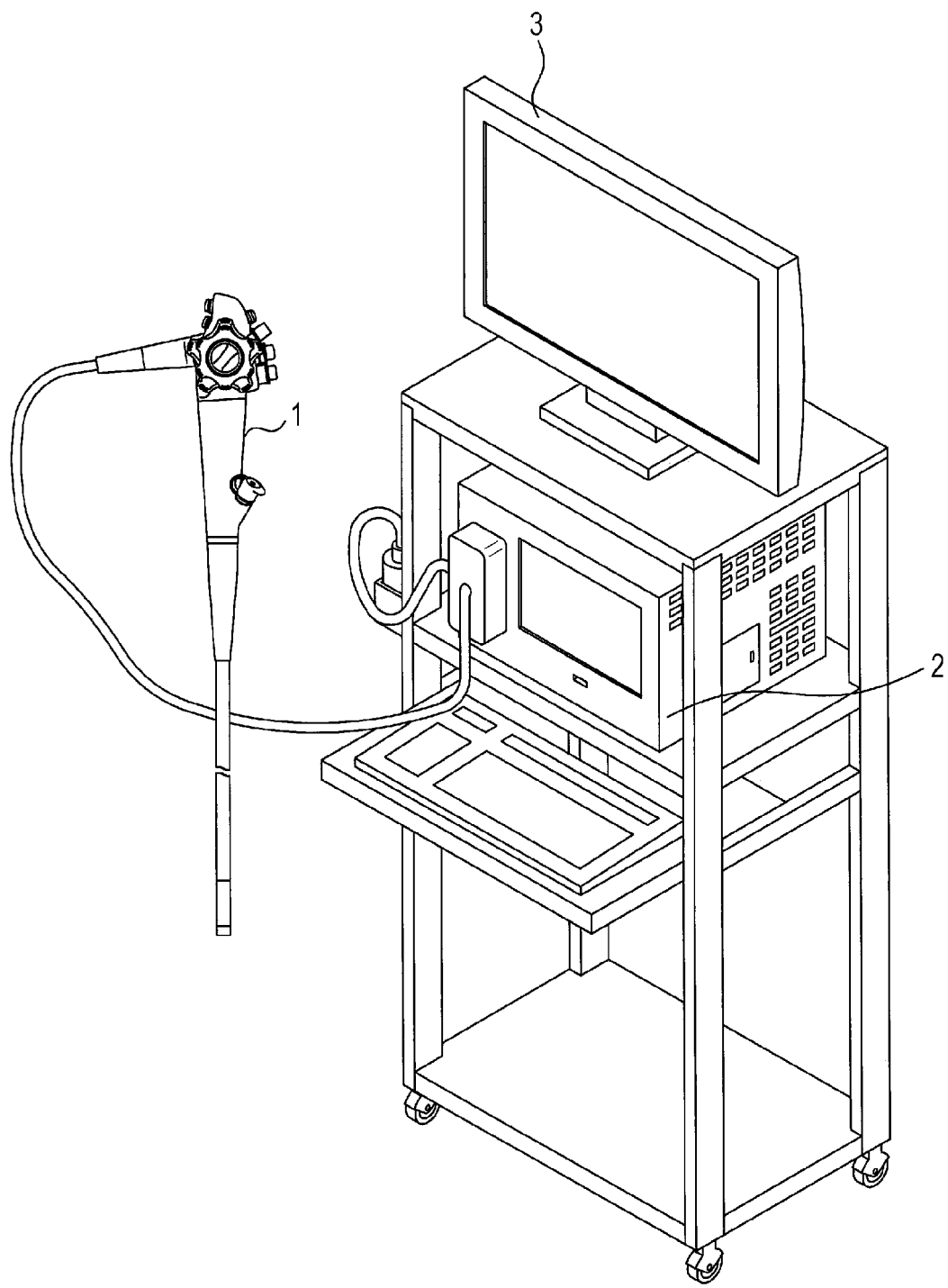
FIG. 1 is a schematic diagram illustrating a configuration example of an endoscope system.

FIG. 1 is a schematic diagram illustrating a configuration example of an endoscope system. The system illustrated in FIG. 1 includes an endoscope 1 which is inserted into a body of a subject to take an image and outputs a video signal of an observation target, an endoscope processor 2 which converts the video signal output by the endoscope 1 to an endoscopic image, and a display device 3 which displays an endoscopic image and the like. Each device transmits and receives electric signals, video signals, etc. via a connector.

The endoscope 1 is an instrument for diagnosing or treating by inserting an insertion portion having an image sensor at the tip portion into the body of a subject. The endoscope 1 transfers a captured image taken by the image sensor at the tip to the processor 2.

The endoscope processor 2 is an information processing device that performs image processing on a captured image taken from the image sensor at the tip of the endoscope 1, generates an endoscopic image, and outputs it to the display device 3. In the following, for the sake of brevity, the endoscope processor 2 will be read as the processor 2.

The display device 3 is a liquid crystal display, an organic electroluminescence (EL) display, or the like, and displays an endoscopic image or the like output from the processor 2.

Figure 2:
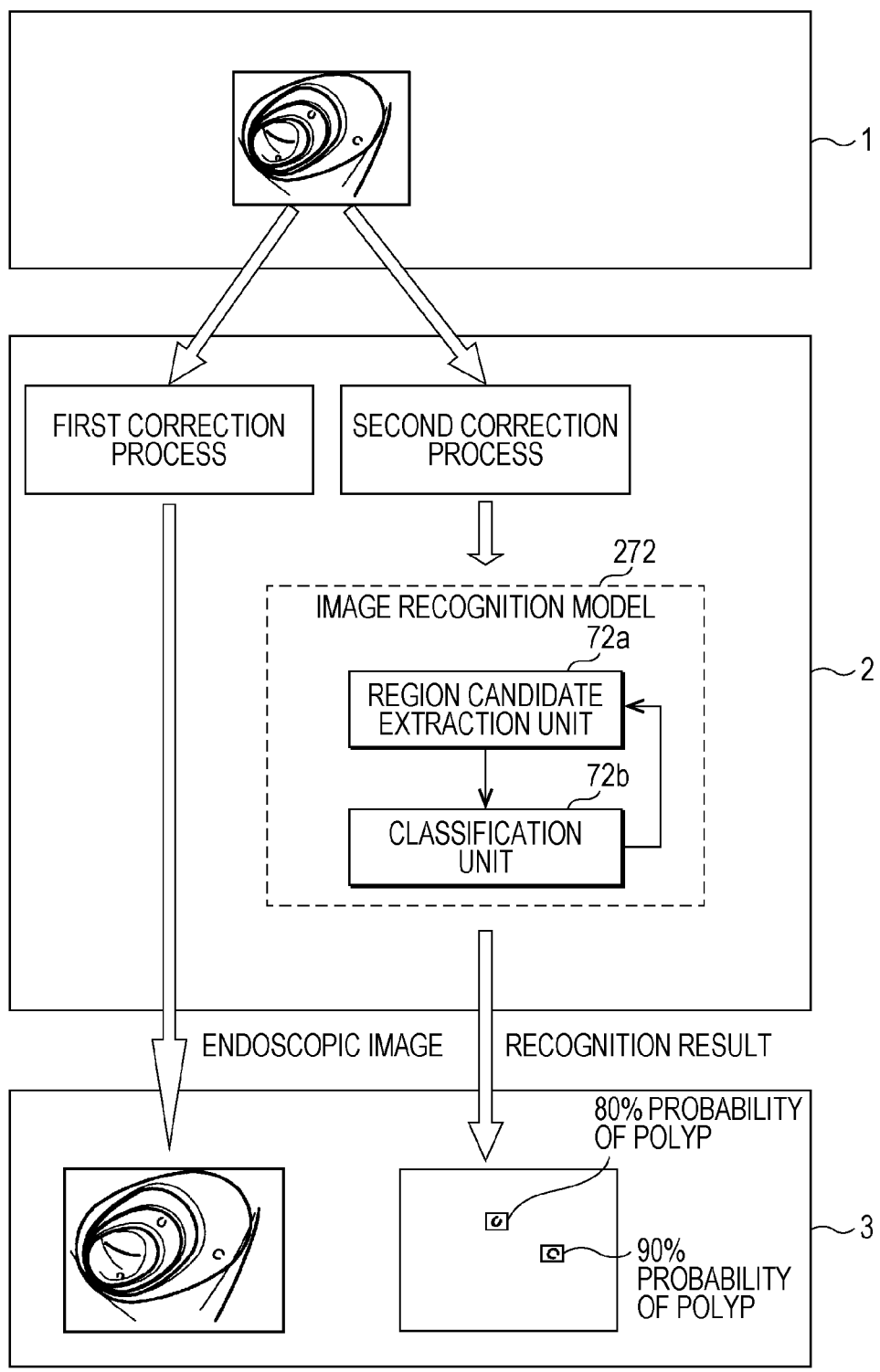
FIG. 2 is an explanatory diagram for explaining a correction process for a captured image taken from an endoscope.

FIG. 2 is an explanatory diagram for explaining a correction process for a captured image taken from the endoscope 1. The processor 2 generates an endoscopic image obtained by correcting the captured image acquired from the endoscope 1 by a first correction process. The processor 2 generates an artificial intelligence (AI) correction image obtained by correcting the captured image acquired from the endoscope 1 by a second correction process. The processor 2 inputs the AI correction image into the image recognition model 272 described later and acquires a recognition result. By using the AI correction image, it is possible to obtain a highly accurate recognition result in an image recognition process by the image recognition model 272. The processor 2 outputs the acquired endoscopic image and the recognition result to the display device 3.

The first correction process is a correction process for generating an endoscopic image suitable for observation by a doctor from a captured image taken from the endoscope 1, and includes at least one of an offset correction process, a gain correction process, a gamma correction process, and a white balance correction process.

An offset correction process removes the influence of the dark current by using offset correction data predetermined based on a dark current image. The dark current is a current that flows when a voltage is applied to an electric element such as a semiconductor exhibiting a photoelectric effect without irradiating light due to a thermal cause, insulation failure, crystal defect, or the like. Noises may appear in the captured image due to the generated dark current. The offset correction data may be generated by acquiring a plurality of dark current image data in a non-capturing period before starting capturing of the object, and synthesizing the plurality of acquired dark current image data. Using the generated offset correction data, a constant dark current value is subtracted from the pixel value of each pixel constituting the captured image obtained from the endoscope 1.

The gain correction process is a process for correcting the sensitivity variation of each pixel of the image sensor. The gamma correction process is a correction process for adjusting the relative relationship between the gradation value of the captured image and the gradation value of the signal output to the display device 3 to display the image as faithful as possible to the original data on the display device 3. In the gamma correction, the shade of the image is corrected to the optimum curve according to the gamma value of an input/output device such as the display device 3.

A white balance correction process is a correction process that accurately expresses the white color of the captured image by adjusting the color balance between blue, red, and green even under light sources having different color temperatures.

The second correction process is a correction process for acquiring a highly accurate recognition result in the image recognition process using the trained image recognition model 272, and includes a basic correction process, a geometric distortion correction process, and a noise uniformization correction process, or a noise reduction process.

The basic correction process includes an offset correction process, a gain correction process, a shading correction process, and a white balance correction process. The shading correction process is a correction process for making the luminosity of the entire captured image uniform. Since the offset correction process, the gain correction process, and the white balance correction process are the same as the offset correction process, the gain correction process, and the white balance correction process of the first correction process, the description thereof will be omitted.

Figure 3:
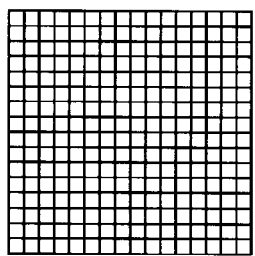
FIG. 3 is an explanatory diagram for explaining a geometric distortion correction process.
Figure 3:
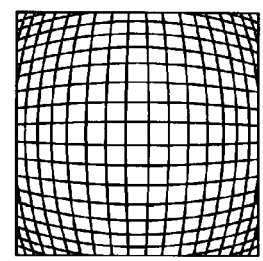
Figure 3:
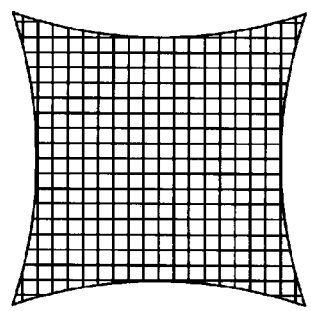
Figure 3:
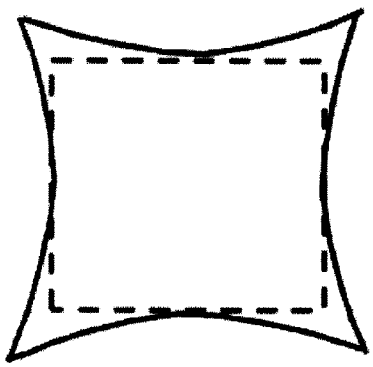
Figure 3:
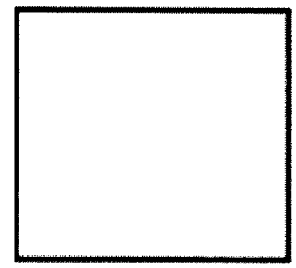
Figure 3:
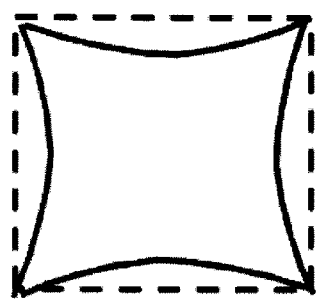
Figure 3:
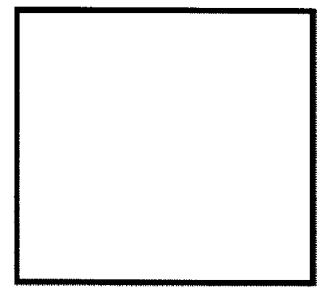
Figure 3:
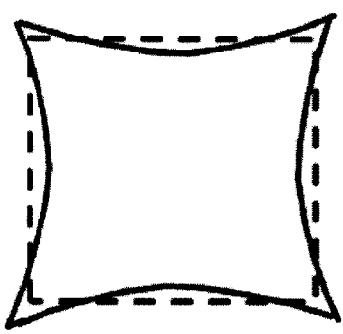
Figure 3:
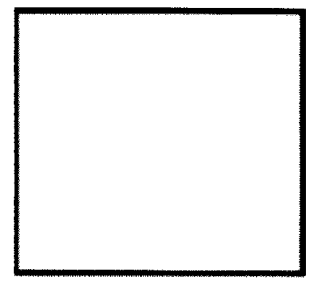

The geometric distortion correction process is a process for correcting the distortion of a captured image. FIG. 3 is an explanatory diagram for explaining the geometric distortion correction process. The upper left side of FIG. 3 illustrates an object having a grid pattern in which vertical lines and horizontal lines are arranged at equal intervals. In the center of the upper part of FIG. 3, a captured image obtained by taking the object taken by the endoscope 1 is illustrated. Due to the geometric distortion caused by the wide-angle lens of the endoscope 1, the central part is bulged and the peripheral part is contracted. The straight line of the object is in a curved state. On the upper right side of FIG. 3, an image corrected from the captured image by geometric distortion correction process is illustrated. The curved line is returned to the original straight line by the geometric distortion correction process.

Since the central part of the captured image is contracted by the geometric distortion correction process, the outer shape of the corrected image becomes a pincushion shape. A rectangular region is acquired from the corrected captured image and used in the subsequent process. In the following description, a rectangle indicating the range for acquiring a region is described as a reference rectangle.

The acquisition process of a reference rectangular region will be described with reference to the lower part of FIG. 3. The first row from the top of the lower part of FIG. 3 illustrates the case where the reference rectangular region is acquired from the inside of the corrected captured image. Specifically, the largest rectangle that fits inside the captured image corrected into the pincushion shape is used as the reference rectangle.

The second row from the top of the lower part of FIG. 3 illustrates an example of acquiring a reference rectangle from the outer edge of the corrected captured image. Specifically, the smallest rectangle that surrounds the captured image corrected into the pincushion shape is used as the reference rectangle. The pixels in the region between the reference rectangle and the corrected captured image are complemented.

The third row from the top in the lower part of FIG. 3 is in the middle of the process of acquiring the above-mentioned two types of reference rectangular regions. A rectangular region is specified for the captured image of the pincushion shape, and the region without the pixel is complemented with pixels to acquire the reference rectangular region. It should be noted that the process is not limited to the process of acquiring the above-mentioned reference rectangular region. For example, the pixels may be complemented first along each side of the captured image of the pincushion shape, and an appropriate rectangular region may be cut out from the complemented region to obtain the reference rectangular region. The smaller the geometric distortion, the higher the accuracy and reproducibility of the feature parameters of the image. It is known that stable results can be output and the recognition rate increases when recognition is performed using the feature parameters of an image with good accuracy.

The noise uniformization correction process equalizes the standard deviation (SD) of noise between the peripheral part and the central part of the captured image. When the standard deviation of the noises in the peripheral part of the captured image is larger than the standard deviation of the noises in the central part, the processor 2 applies a smoothing filter, a median filter, or the like to the pixels in the peripheral part to make the standard deviation of noises of the central part and the periphery equivalent. The noise reduction process reduces the overall noises of the captured image. Even if the noise uniformization is not very good, it is sufficient if the overall noise can be reduced.

In image recognition based on AI, it has been known that the accurate of the feature parameter of the image is improved, the recognition result can be output with high accuracy, and a recognition rate is increased in the less noise, the better noise uniformization, the less shading, and the less geometric distortion, the less variation of each pixel, and the linear gradation conversion instead of the gamma correction fitted to the characteristics of human eyes compared to the case of visual observation. Therefore, the visual image and the image for image recognition based on AI are corrected separately.

Figure 4:
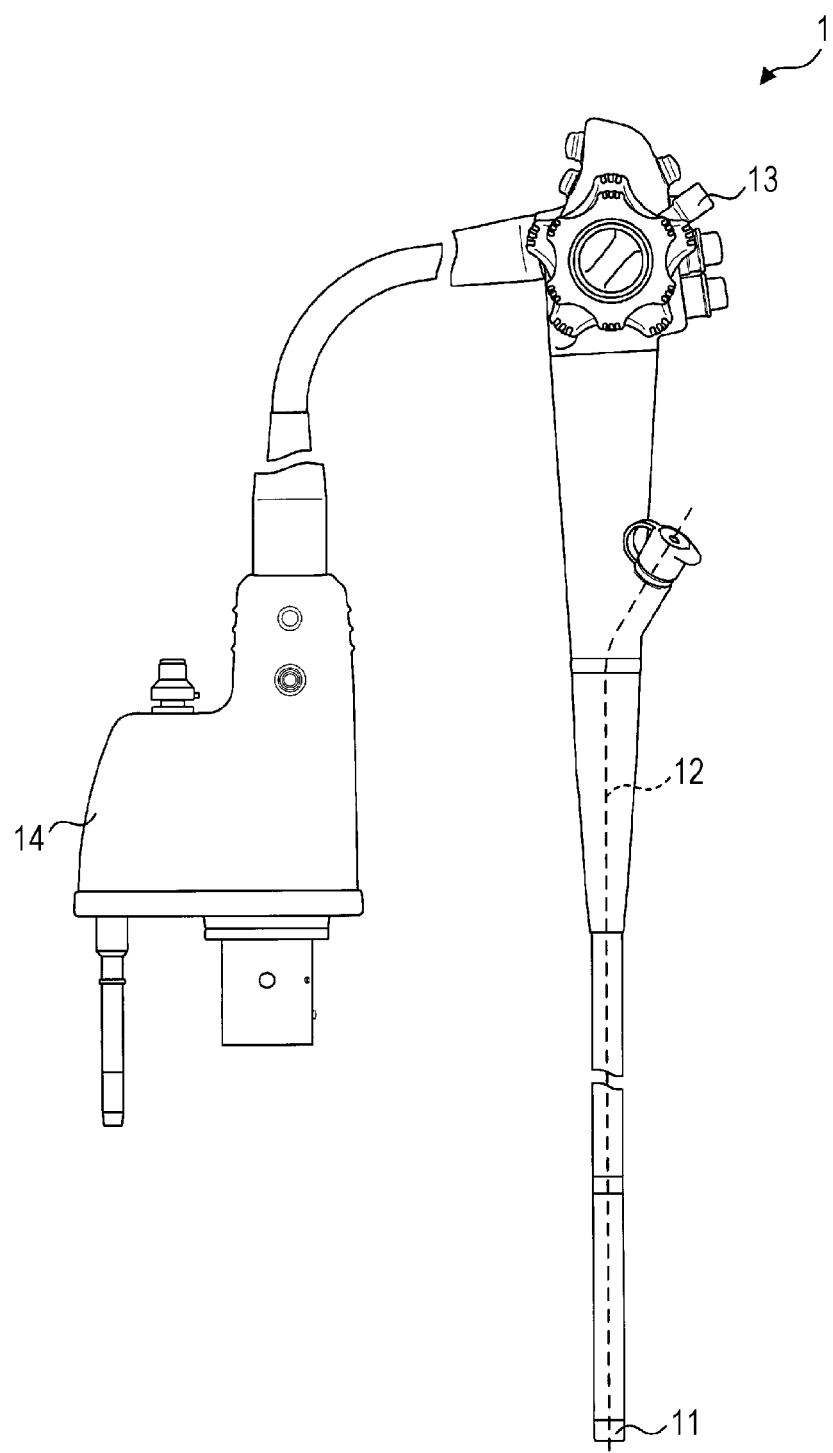
FIG. 4 is an exterior view of an endoscope.

FIG. 4 is an exterior view of the endoscope 1. The endoscope 1 includes an image sensor 11, a treatment tool insertion channel 12, an operation unit 13, and a connector 14. The image sensor 11 is, for example, a CCD image sensor, a CMD image sensor, or a CMOS image sensor installed at the tip portion of the endoscope 1, and performs photoelectric conversion of the incident light. An electric signal generated by the photoelectric conversion is subjected to signal processing such as A/D conversion and noise removal by a signal processing circuit (not illustrated), and is output to the processor 2.

The treatment tool insertion channel 12 is a channel for passing the treatment tool. Treatment tools include, for example, grippers, biopsy needles, forceps, snares, clamps, scissors, scalpels, incision instruments, endoscopic staplers, tissue loops, clip pliers, suture delivery instruments, or energy-based tissue clotting instruments or tissue cutting instruments. The operation unit 13 is provided with a release button, an angle knob for bending the tip of the endoscope, and the like, and receives operation instruction signals of peripheral devices such as air supply, water supply, and gas supply. The connector 14 is connected to the processor 2.

Figure 5:
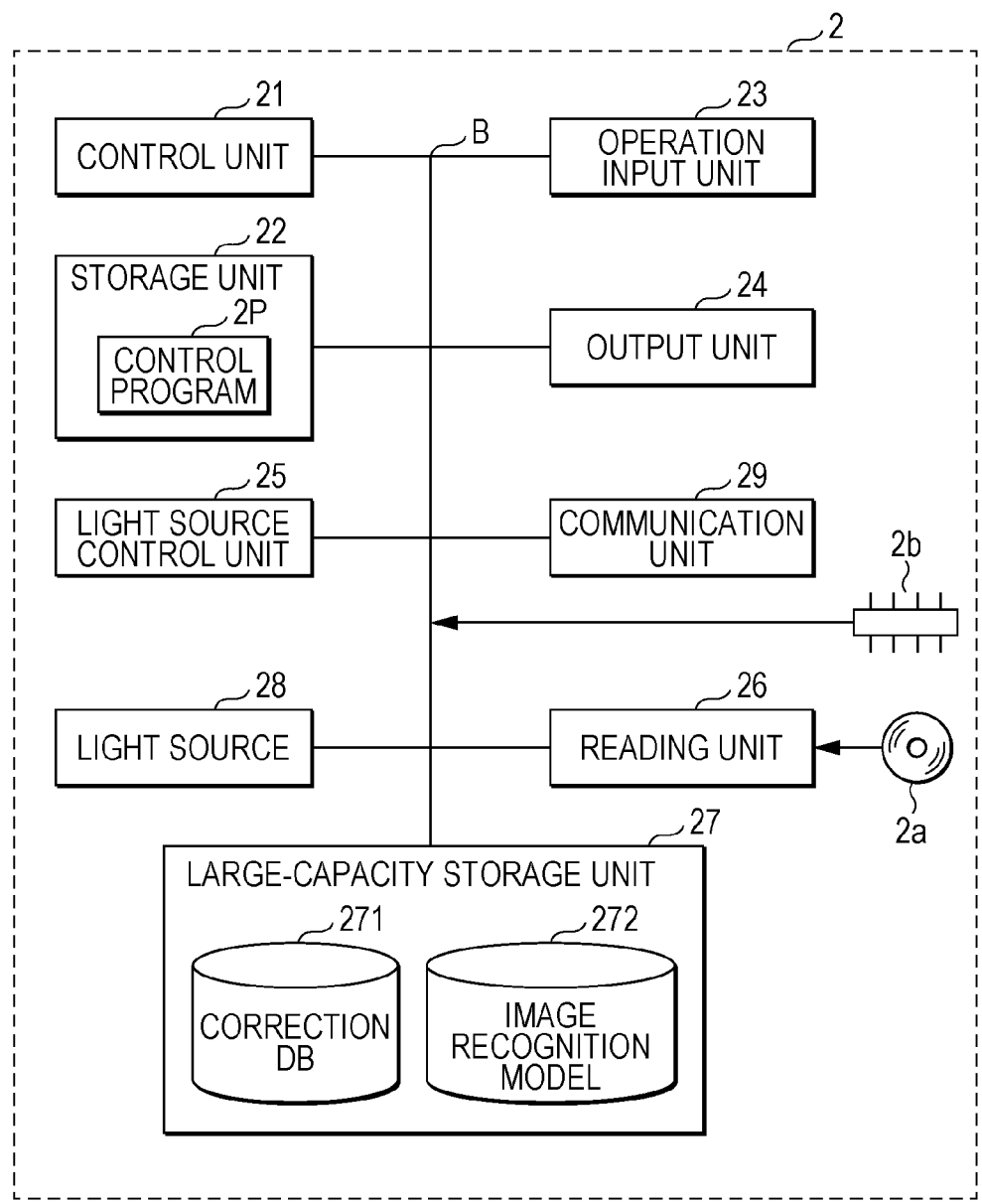
FIG. 5 is a block diagram illustrating a configuration example of a processor.

FIG. 5 is a block diagram illustrating a configuration example of the processor 2. The processor 2 includes a control unit 21, a storage unit 22, an operation input unit 23, an output unit 24, a light source control unit 25, a reading unit 26, a large-capacity storage unit 27, a light source 28, and a communication unit 29. Each configuration is connected by a bus B.

The control unit 21 includes arithmetic processing devices such as a central processing unit (CPU), a micro-processing unit (MPU), and a graphics processing unit (GPU), and reads and executes a control program 2P stored in the storage unit 22 so as to perform various information processing, control processing, and the like related to the processor 2. Although the control unit 21 is described as a single processor in FIG. 5, it may be a multiprocessor.

The storage unit 22 includes memory elements such as a random access memory (RAM) and a read only memory (ROM), and stores the control program 2P or data required for the control unit 21 to execute processing. In addition, the storage unit 22 temporarily stores data and the like necessary for the control unit 21 to execute arithmetic processing. The operation input unit 23 is configured by input devices such as a touch panel and various switches, and inputs an input signal generated in response to an external operation on these input devices to the control unit 21. Under the control of the control unit 21, the output unit 24 outputs an image signal for display and various types of information to the display device 3 to display the image and information.

The light source control unit 25 controls the amount of light emitted from the illumination light by turning on/off an LED and the like and by adjusting the drive current and the drive voltage of the LED and the like. Further, the light source control unit 25 controls the wavelength band of the illumination light by changing an optical filter or the like. The light source control unit 25 adjusts an emission timing, an emission period, the amount of light, and a spectral spectrum of the illumination light by independently controlling the lighting and extinguishing of each LED and the amount of light emitted at the time of lighting.

The reading unit 26 reads a portable storage medium 2a including a compact disc (CD)-ROM or a digital versatile disc (DVD)-ROM. The control unit 21 may read the control program 2P from the portable storage medium 2a via the reading unit 26 and store it in the large-capacity storage unit 27. Further, the control unit 21 may download the control program 2P from another computer via a network N or the like and store it in the large-capacity storage unit 27. Furthermore, the control unit 21 may read the control program 2P from a semiconductor memory 2b.

The large-capacity storage unit 27 includes, for example, a recording medium such as a hard disk drive (HDD) or a solid state drive (SSD). A correction DB 271 and the image recognition model 272 are stored in the large-capacity storage unit 27. The correction DB 271 stores correction data for performing correction process on the captured image taken from the endoscope 1. The image recognition model 272 is an image recognizer that recognizes lesions, tissues, etc. in the body of a subject based on the captured image, and is a trained model generated by machine learning. The image recognition model 272 may be arranged and used in a cloud computing system connected via a network.

In this embodiment, the storage unit 22 and the large-capacity storage unit 27 may be configured as an integrated storage device. Further, the large-capacity storage unit 27 may be configured by a plurality of storage devices. Furthermore, the large-capacity storage unit 27 may be an external storage device connected to the processor 2.

The light source 28 includes a light source that emits illumination light used for illuminating the observation target. The light source is, for example, a semiconductor light source such as a multi-color light emitting diode (LED) having a different wavelength range, a combination of a laser diode and a phosphor, a xenon lamp, a halogen lamp, or the like. The light source 28 adjusts the luminosity and the like according to the control from the light source control unit 25 of the processor 2. In this embodiment, the processor 2 is an integrated type of light source, but the present invention is not limited to this. For example, the processor 2 may be a light source separation type that is separated from the light source device. The communication unit 29 is a communication module for performing processing related to communication, and transmits/receives information to/from an external information processing device or the like via the network N.

Figures 6, 7:
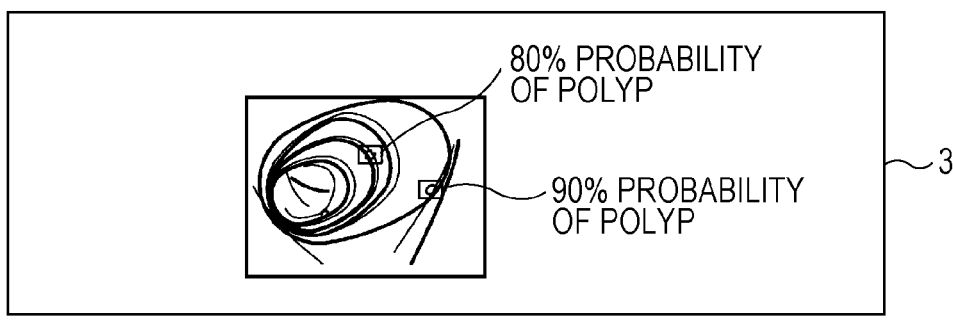
FIG. 6 is an explanatory diagram illustrating an example of a record layout of a correction DB.
FIG. 7 is a schematic diagram for displaying an endoscopic image and a recognition result.

FIG. 6 is an explanatory diagram illustrating an example of a record layout of the correction DB 271. The correction DB 271 includes a management ID column, a correction type column, and a correction data column. The management ID column stores the ID of the correction data which is uniquely specified in order to identify each correction data. The correction type column stores the type of correction data. The correction data column stores various correction data according to the endoscope 1 and the display device 3 used in combination with the processor 2. For example, the correction data for offset correction is a correction coefficient for correcting the offset. For example, the correction data of gamma correction is a table in which the gamma curves of the combination display device 3 are recorded.

Next, returning to FIG. 2, the correction process for the captured image taken from the endoscope 1 will be described in detail. When the tip of the endoscope 1 is inserted into the body of the subject, the control unit 21 of the processor 2 acquires a captured image taken from the image sensor 11 at the tip of the endoscope 1. The control unit 21 corrects the captured image acquired from the endoscope 1 by the first correction process.

Specifically, the control unit 21 of the processor 2 performs the offset correction process on the acquired captured image, and performs gain correction on the captured image after offset correction. The control unit 21 performs the gamma correction process on the image after gain correction, and performs the white balance correction process on the captured image after gamma correction. The order of the correction processes described above is not limited. For example, the control unit 21 may perform the first correction process in the order of offset correction, gain correction, white balance correction, and gamma correction. Also, all corrections are not always essential. At least one may be done partially. As described above, the control unit 21 generates an endoscopic image.

In parallel with the first correction process, the control unit 21 corrects the captured image acquired from the endoscope 1 by the second correction process to generate an AI correction image. Specifically, the control unit 21 performs a second correction process on the acquired captured image in the order of basic correction, geometric distortion correction, noise uniformization correction, or noise reduction processing. The basic correction process includes a gain correction process, a shading correction process, and a white balance correction process. The control unit 21 performs the basic correction process in the order of gain correction, shading correction, and white balance correction, or in the order of gain correction, white balance correction, and shading correction.

In addition, all corrections are not always essential, and partial corrections may be performed. Specifically, for example, the control unit 21 may perform a second correction process in the order of basic correction, noise uniformization correction or noise reduction processing, and geometric distortion correction. Further, the control unit 21 may perform the second correction process in the order of geometric distortion correction, basic correction, noise uniformization correction, or noise reduction processing. That is, the execution order is not limited to the second correction process of the basic correction, the geometric distortion correction, the noise uniformization correction, or the noise reduction processing, and any order or combination may be used. Furthermore, it may be a second correction process (fourth embodiment) that is partially performed, which will be described later.

The control unit 21 inputs an AI correction image into the trained image recognition model 272, which will be described later, and acquires an image recognition result.

In the following, an example of outputting the recognition result of recognizing a polyp in the large intestine by using the image recognition model 272 (an image recognition model based on AI (artificial intelligence)) constructed by deep learning will be described. A polyp is a part of the mucous membrane of the large intestine that rises like a wart and protrudes into the space of the large intestine. Most of the polyps are benign diseases, and do not cause any harm to the body immediately, but if they grow gradually, they may cause bleeding. In this embodiment, an example of the image recognition model 272 for polyp extraction will be described, but other trained image recognition models may be used.

The image recognition model 272 is used as a program module that is a part of artificial intelligence software. The image recognition model 272 is a learning model that outputs information indicating a region in which a polyp is estimated to appear and a probability that a polyp appears in that region when an AI correction image is input.

The image recognition model 272 is a neural network generated by supervised learning. The training data is data in which the coordinate range of the image region corresponding to the polyp and the information about the polyp are labeled with respect to the AI correction image. The image recognition model 272 generated by an information processing device (for example, a server) (not illustrated) may be stored in the large-capacity storage unit 27 via a network or the reading unit 26.

The image recognition model 272 of this embodiment performs estimation using regions with convolutional neural network (RCNN). The image recognition model 272 includes a region candidate extraction unit 72a and a classification unit 72b. The classification unit 72b includes a neural network (not illustrated). The neural network includes a convolution layer, a pooling layer, and a fully-connected layer.

The captured image is input to the image recognition model 272. The region candidate extraction unit 72a extracts various sizes of region candidates from the captured image. The classification unit 72b calculates the feature amount of the extracted region candidate, and classifies whether the object reflected in the region candidate is a polyp based on the calculated feature amount. The image recognition model 272 repeats the extraction and classification of region candidates.

The image recognition model 272 outputs the range of the region and the probability that the polyp appears for the region candidate classified as having the polyp appeared with a probability higher than a predetermined threshold. In the example illustrated in FIG. 2, a region in which a polyp appears with an 80% probability and a region in which a polyp appears with a 90% probability are detected.

Instead of RCNN, any object detection algorithm such as Fast RCNN, Faster RCNN or single shot multibook detector (SSD), you only look once (YOLO) may be used.

The control unit 21 generates an image for display by superimposing the recognition result output from the trained image recognition model 272 with the endoscopic image based on the captured image subjected to the first correction process and the AI correction image subjected to the second correction process. The control unit 21 outputs the generated display image to the display device 3. Although the examples of the first correction process and the second correction process for the captured image in the large intestine have been described above, the present invention is not limited to this, and the first correction process and the second correction process for other parts may be performed. Other sites are, for example, the stomach, duodenum, bronchi, or urinary system.

FIG. 7 is a schematic diagram for displaying the endoscopic image and the recognition result. As illustrated in the drawing, the display device 3 displays an image for display output from the processor 2. The recognition result may be, for example, the probability of an ulcer or a tumor. The display method is not limited to the above. For example, an identification ID may be assigned to the recognized polyp, and the recognition result may be displayed in a region other than the endoscopic image for each identification ID.

Figure 8:
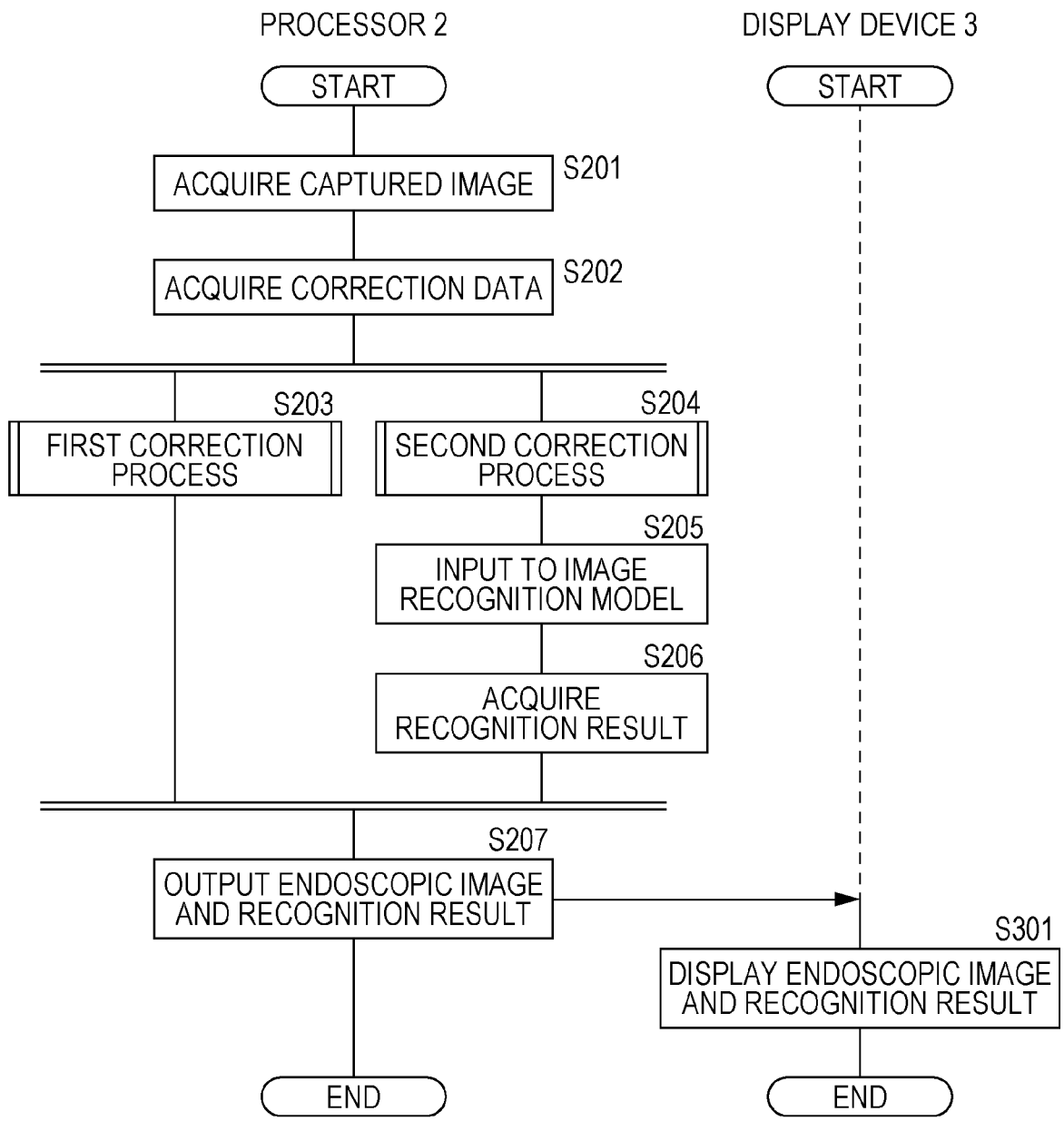
FIG. 8 is a flowchart illustrating a processing procedure when performing a correction process on a captured image.

FIG. 8 is a flowchart illustrating a processing procedure when performing a correction process on a captured image. The control unit 21 of the processor 2 acquires the captured image transferred from the endoscope 1 (step S201). The control unit 21 acquires correction data (coefficients) for performing various correction processes from the correction DB 271 of the large-capacity storage unit 27 (step S202). The correction data may be, for example, offset correction data, shading correction coefficient, or the like.

The control unit 21 performs the first correction process on the acquired captured image (step S203). The subroutine of the first correction process will be described later. At the same time, the control unit 21 performs the second correction process on the acquired captured image to generate an AI correction image (step S204). The subroutine of the second correction process will be described later.

Note that FIG. 8 has described an example in which the first correction process and the second correction process are performed in parallel, but the present invention is not limited to this. One of the first correction process and the second correction process may be executed first and the other may be executed later.

The control unit 21 inputs the AI correction image corrected by the second correction process to the trained image recognition model 272 (step S205). The control unit 21 extracts the image feature amount for the AI correction image uses the image recognition model 272 so as to acquire the recognition result of recognizing a lesion (for example, colorectal polyp or the like) (step S206).

The control unit 21 outputs the endoscopic image generated in step S203 and the recognition result by the image recognition model 272 acquired in step S206 to the display device 3 (step S207), and the control unit 21 ends the process. The display device 3 displays the endoscopic image and the recognition result output from the processor 2 (step S301).

Figure 9:
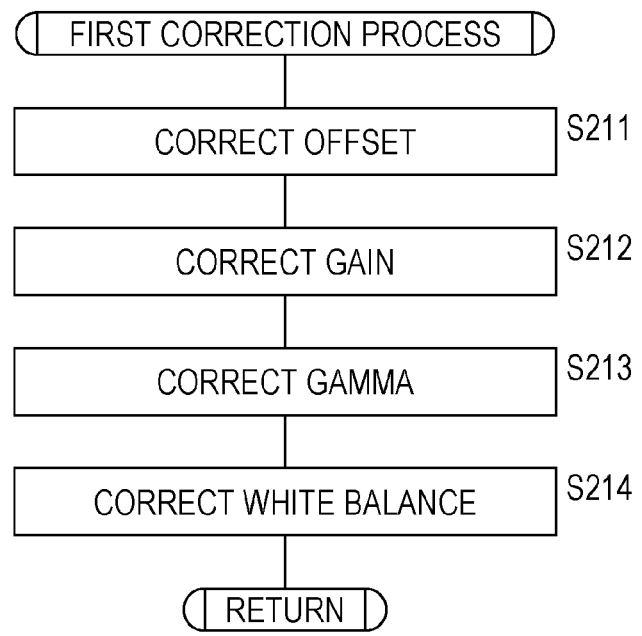
FIG. 9 is a flowchart illustrating a processing procedure of a subroutine of a first correction process.

FIG. 9 is a flowchart illustrating the processing procedure of the subroutine of the first correction process. The control unit 21 of the processor 2 performs the offset correction process on the captured image taken from the endoscope 1 using the offset correction data acquired from the correction DB 271 (step S211), and removes the dark current. The control unit 21 multiplies each pixel of the captured image after offset correction by the gain correction coefficient acquired from the correction DB 271 to perform the gain correction process (step S212). The control unit 21 performs the gamma correction process based on the gamma value of the display device 3 (step S213). The control unit 21 calibrates the RGB signal level of each pixel value of the captured image after gamma correction using the RGB correction coefficient of the white balance correction acquired from the correction DB 271, and performs the white balance correction process (step S214). After that, the control unit 21 ends the process. The order of each correction process illustrated in FIG. 9 can be changed as appropriate.

Figure 10:
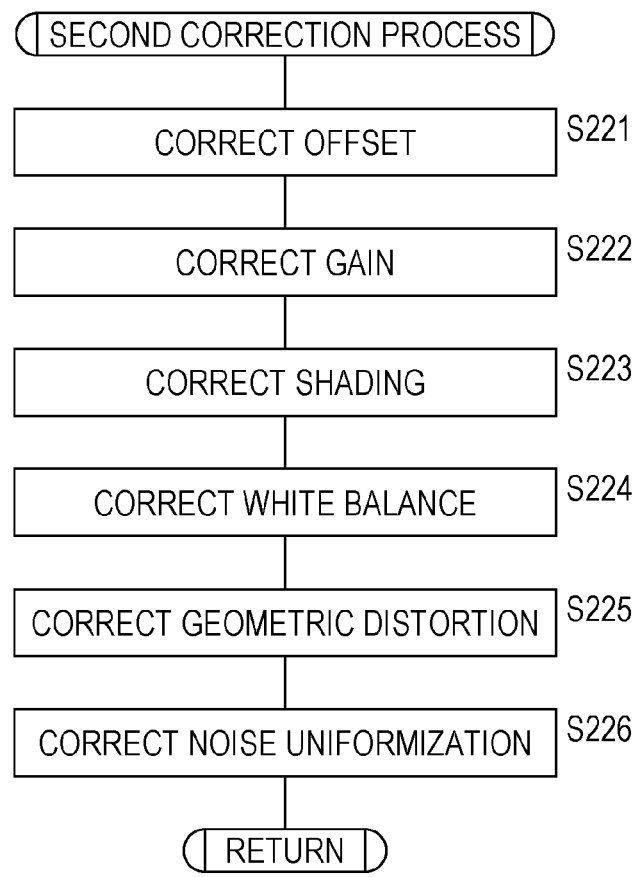
FIG. 10 is a flowchart illustrating a processing procedure of a subroutine of a second correction process.

FIG. 10 is a flowchart illustrating the processing procedure of the subroutine of the second correction process. The control unit 21 of the processor 2 performs the offset correction process on the captured image taken from the endoscope 1 using the offset correction data acquired from the correction DB 271 (step S221), and removes the dark current. The control unit 21 multiplies each pixel of the captured image after offset correction by the gain correction coefficient acquired from the correction DB 271 to perform the gain correction process (step S222).

The control unit 21 multiplies each pixel of the captured image after gain correction by the shading correction coefficient acquired from the correction DB 271 to perform the shading correction process (step S223). The control unit 21 calibrates the RGB signal level of each pixel value of the captured image after shading correction using the RGB correction coefficient of the white balance correction acquired from the correction DB 271, and performs the white balance correction process (step S224). In FIG. 10, the control unit 21 performs the correction process in the order of shading correction and white balance correction, but the present invention is not limited to this. For example, the control unit 21 may perform the correction process in the order of white balance correction and shading correction.

The control unit 21 performs the geometric distortion correction process so that all pixels of the captured image after white balance correction are evenly spaced (step S225). The control unit 21 calculates the standard deviation of noises in the peripheral part and the central part of the captured image after the geometric distortion correction. When the standard deviation of noises of the peripheral part is larger than the standard deviation of noises of the central part, the control unit 21 applies a smoothing filter, a median filter, or the like to perform the noise uniformization correction process (step S226). After that, the control unit 21 ends the process.

According to this embodiment, it is possible to generate an endoscopic image suitable for observation by a doctor by performing the first correction process on the captured image taken from the endoscope 1.

According to this embodiment, by performing the second correction process on the captured image taken from the endoscope 1, the accuracy of image recognition is improved when the corrected captured image is input to the trained image recognition model. Therefore, it is possible to output a highly accurate image recognition result.

According to this embodiment, it is possible to support a doctor's endoscopic diagnosis by superimposing and outputting a captured image for optimized observation and a highly accurate image recognition result using a trained image recognition model.

Second Embodiment

The second embodiment relates to a mode in which a selection of a trained image recognition model to be used is accepted from a plurality of trained image recognition models. The description of the contents overlapping with the first embodiment will be omitted.

Figure 11:
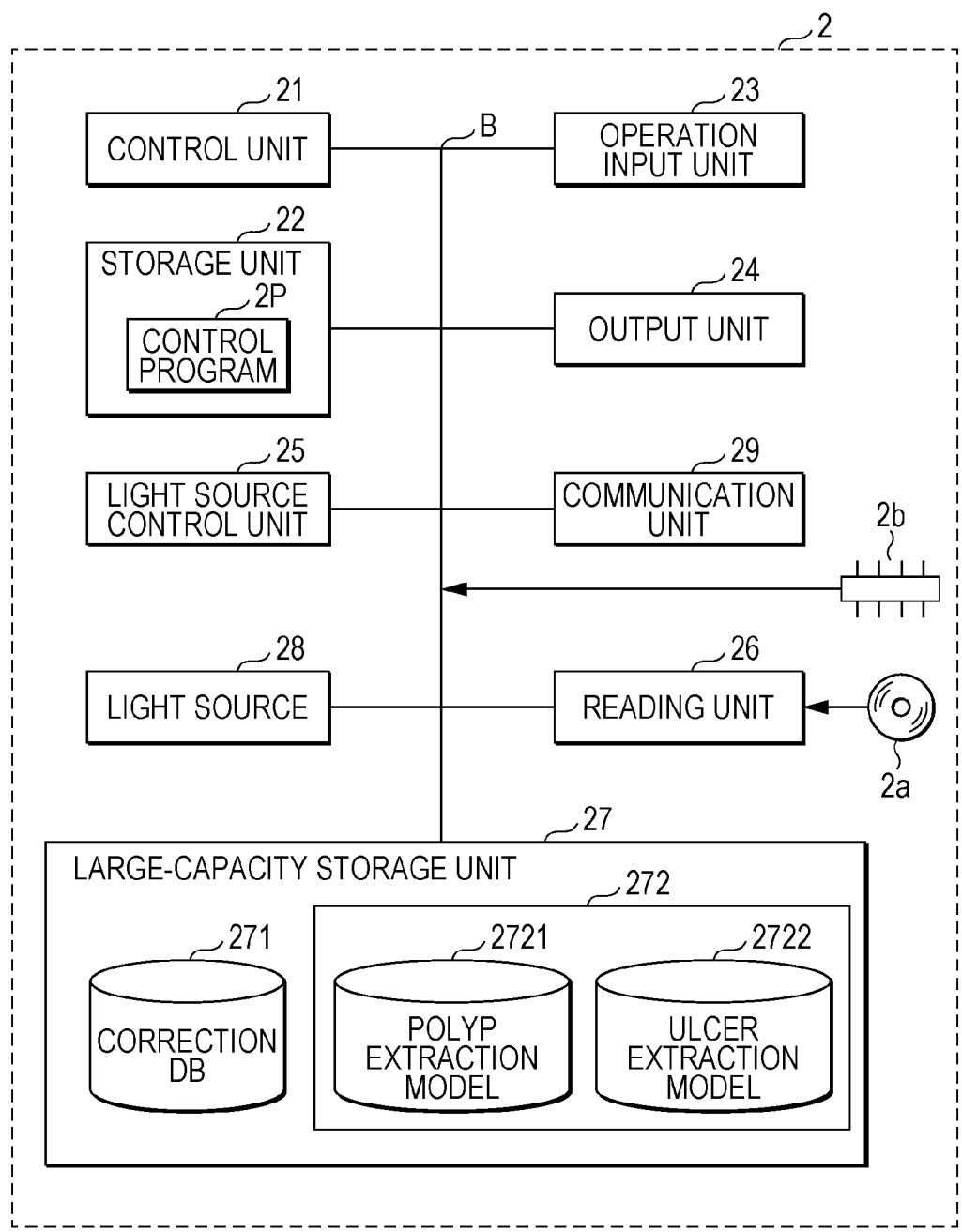
FIG. 11 is a block diagram illustrating a configuration example of a processor of a second embodiment.

FIG. 11 is a block diagram illustrating a configuration example of the processor 2 of the second embodiment. The contents overlapping with FIG. 5 are designated by the same reference numerals and the description thereof will be omitted. In this embodiment, the image recognition model 272 describes an example of the polyp extraction model 2721 and the ulcer extraction model 2722. The type and quantity of the image recognition model 272 are not particularly limited. Further, the processor 2 downloads the image recognition model 272 from an external information processing device (not illustrated) and stores it in the large-capacity storage unit 27. The processor 2 may download the image recognition model 272 selected by the user from a large number of image recognition models 272 stored in the external information processing device. The polyp extraction model 2721 is an extractor that extracts polyps in the large intestine, and is a trained model generated by machine learning. The ulcer extraction model 2722 is an extractor that extracts ulcers and is a trained model generated by machine learning.

Figure 12:
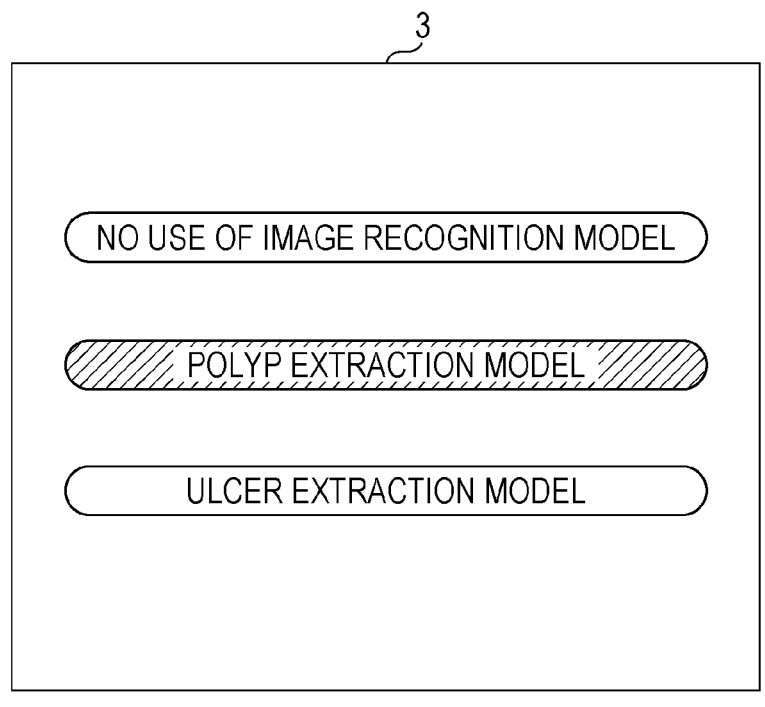
FIG. 12 is an example of a screen that accepts selection of a trained image recognition model.
Figure 12:
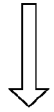
Figure 12:
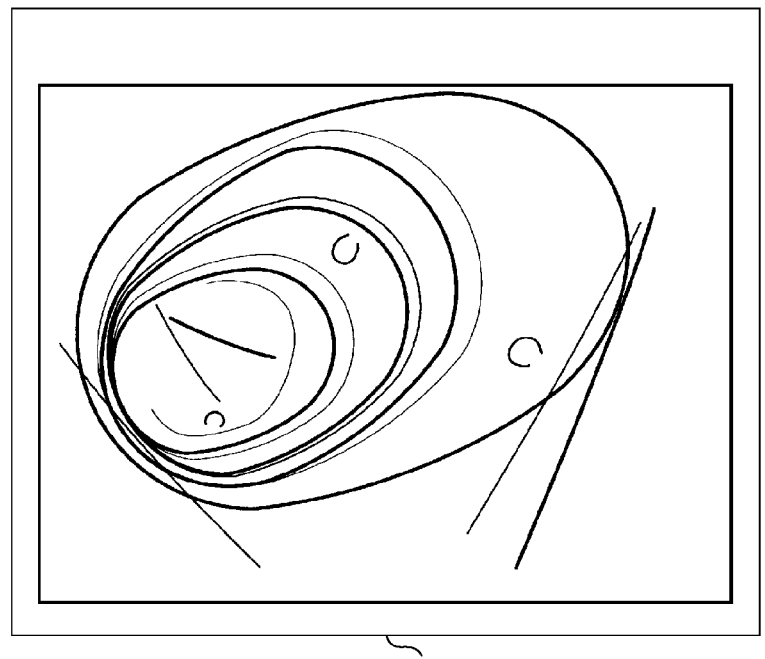

FIG. 12 illustrates an example of a screen that accepts the selection of the trained image recognition model. The control unit 21 of the processor 2 outputs the names of a plurality of trained and selectable image recognition models to the display device 3. As illustrated in the drawing, buttons for selecting "no use of image recognition model", "polyp extraction model", and "ulcer extraction model" are displayed.

When the control unit 21 accepts the selection of "no use of image recognition model" by the operation input unit 23, the control unit 21 performs only the first correction process on the captured image taken from the endoscope 1, and outputs the endoscopic image based on the captured image corrected by the first correction process to the display device 3.

When the control unit 21 accepts the selection of the "polyp extraction model" or the "ulcer extraction model" by the operation input unit 23, the control unit 21 performs the first correction process and the second correction process on the captured image taken from the endoscope 1. The "polyp extraction model" is a selection mode that accepts a process of outputting a recognition result of recognizing an image when the captured image taken from the endoscope 1 is input to the polyp extraction model 2721. The "ulcer extraction model" is a selection mode that accepts a process of outputting a recognition result of recognizing an image when the captured image taken from the endoscope 1 is input to the ulcer extraction model 2722.

For example, when the control unit 21 accepts the selection of the "polyp extraction model" by the operation input unit 23, the control unit 21 inputs the captured image corrected by the second correction process into the polyp extraction model 2721, and outputs the recognition result of recognizing the captured image using the polyp extraction model 2721. The control unit 21 superimposes the endoscopic image and the recognition result using the polyp extraction model 2721 to generate an image for display. The control unit 21 outputs the generated display image to the display device 3.

Figure 13:
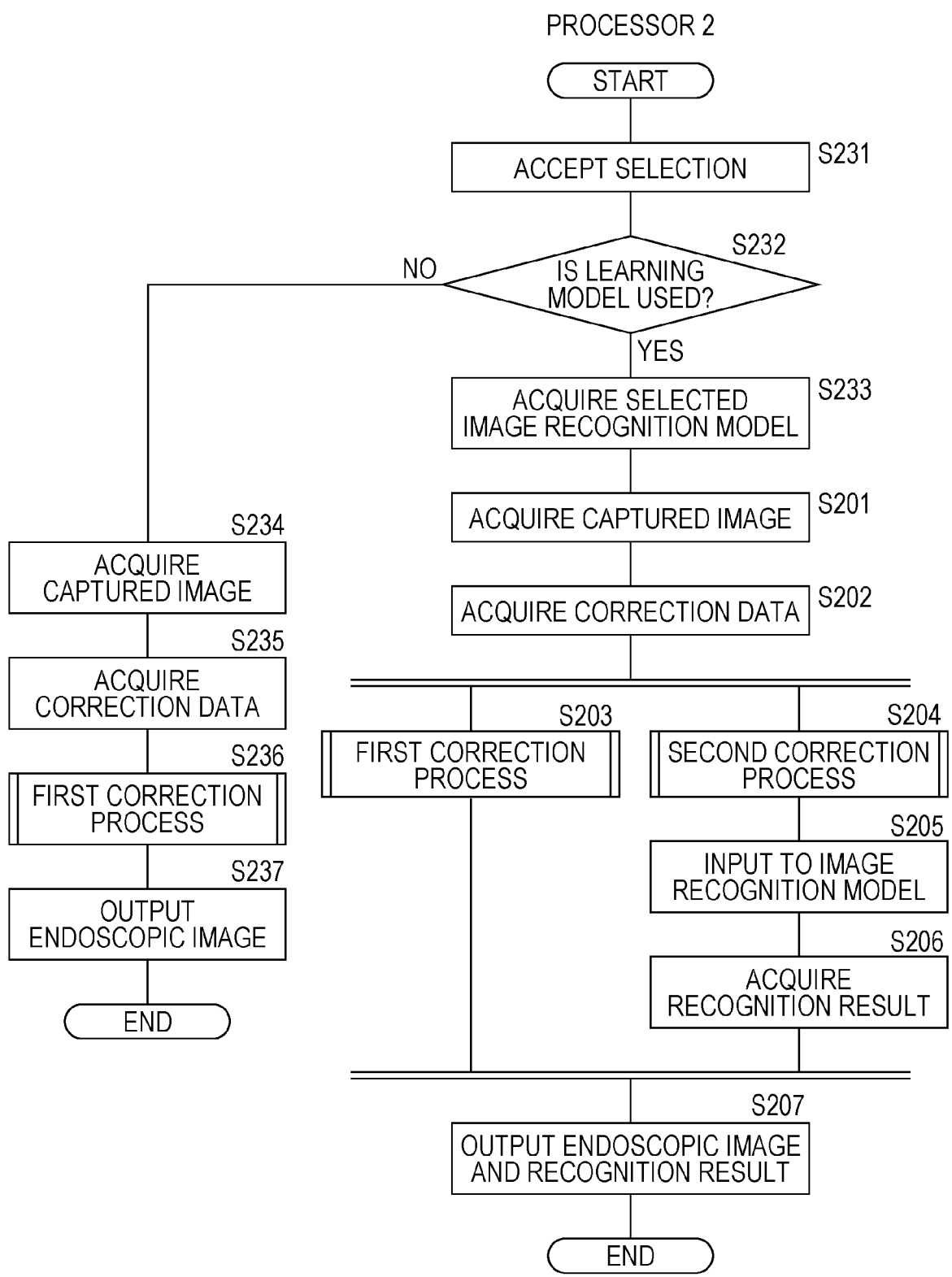
FIG. 13 is a flowchart illustrating a processing procedure when accepting selection of a trained image recognition model.

FIG. 13 is a flowchart illustrating a processing procedure when accepting the selection of a trained image recognition model. The contents overlapping with FIG. 8 are designated by the same reference numerals and the description thereof will be omitted. The control unit 21 of the processor 2 accepts a selection from a doctor by the operation input unit 23 (step S231). The control unit 21 determines whether the trained image recognition model has been used based on the accepted selection (step S232). When the control unit 21 determines that the trained image recognition model has been used (YES in step S232), the control unit 21 acquires the trained image recognition model selected from the large-capacity storage unit 27 according to a user's selection (step S233), and executes step S201.

When the control unit 21 determines that the trained image recognition model is not used (NO in step S232), the control unit 21 acquires the captured image taken from the endoscope 1 (step S234). The control unit 21 acquires correction data (coefficients) for performing various correction processes from the correction DB 271 of the large-capacity storage unit 27 (step S235). The control unit 21 performs the first correction process on the acquired captured image (step S236), and outputs the endoscopic image based on the captured image corrected by the first correction process to the display device 3 (step S237). The control unit 21 ends the process.

According to this embodiment, it is possible to select a trained image recognition model to be used by a doctor from a plurality of trained image recognition models.

According to this embodiment, it is possible to freely switch between the use mode of the image recognition model and the non-use mode of the image recognition model.

Third Embodiment

Figure 14:
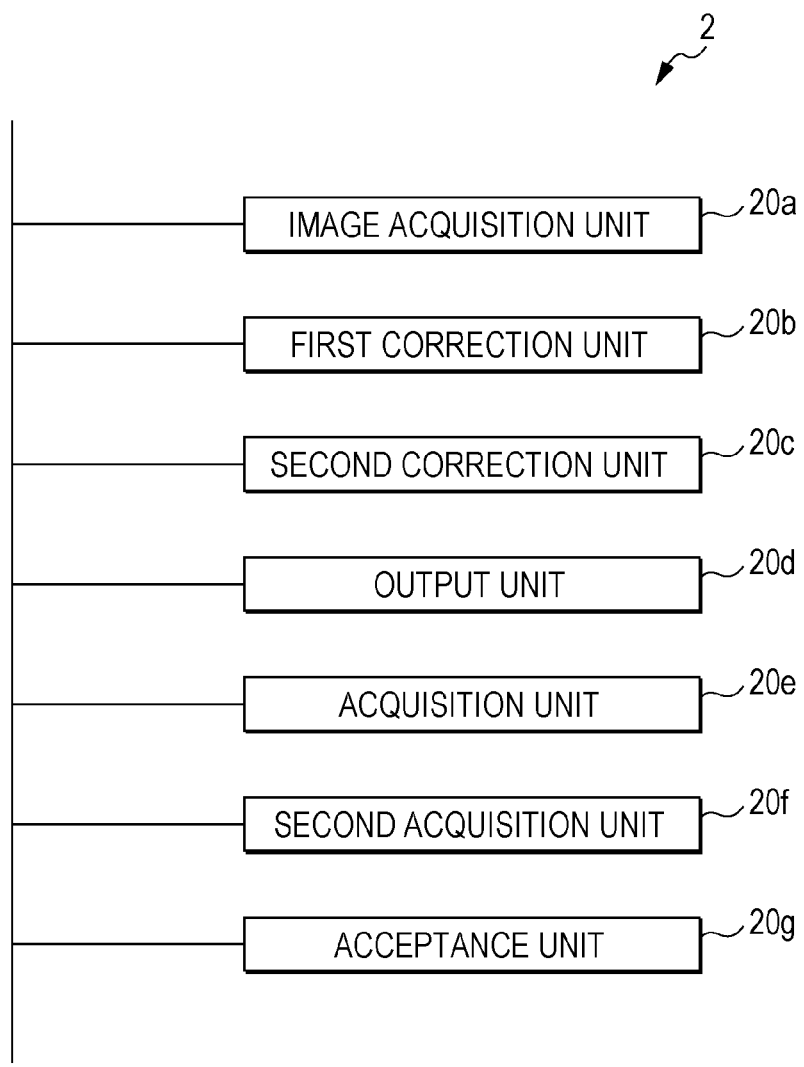
FIG. 14 is a functional block diagram illustrating the operation of the processors of the first and second embodiments.

FIG. 14 is a functional block diagram illustrating the operation of the processor 2 of the above-mentioned embodiment. When the control unit 21 executes the control program 2P, the processor 2 operates as follows.

The image acquisition unit 20a acquires a captured image from the endoscope 1. A first correction unit 20b corrects the captured image acquired by the image acquisition unit 20a by the first correction process. A second correction unit 20c corrects the captured image acquired by the image acquisition unit 20a by the second correction process. The output unit 20d outputs the endoscopic image based on the captured image corrected by the first correction unit 20b and the recognition result of recognizing an image using the trained image recognition model 272 which outputs the recognition result when the captured image corrected by the second correction unit 20c is input.

After the second correction unit 20c corrects the captured image by the geometric distortion correction process, the acquisition unit 20e removes the peripheral portion and acquires the reference rectangular region. In a second acquisition unit 20f, after the second correction unit 20c corrects the captured image by the geometric distortion correction process, the pixels are complemented along each side of the corrected captured image to acquire the reference rectangular region. An acceptance unit 20g accepts the selection of the trained image recognition model to be used from a plurality of trained image recognition models.

Since the third embodiment is as described above and the other parts are the same as those of the first and second embodiments, the corresponding parts are designated by the same reference numerals and detailed description thereof will be omitted.

Fourth Embodiment

The fourth embodiment relates to a mode in which the geometric distortion correction process is performed on a captured image taken from the endoscope and then the image recognition process is performed. The description of the contents overlapping with the first to third embodiments will be omitted.

When the tip of the endoscope 1 is inserted into the body of the subject, the control unit 21 of the processor 2 acquires a captured image taken from the image sensor 11 at the tip of the endoscope 1. The control unit 21 corrects the captured image acquired from the endoscope 1 by the first correction process to generate an endoscopic image. Since the details of the first correction process are the same as those in the first embodiment, the description thereof will be omitted.

In parallel with the first correction process, the control unit 21 corrects the captured image acquired from the endoscope 1 by the second correction process, which is the geometric distortion correction process, to generate an AI correction image. The control unit 21 inputs an AI correction image into the trained image recognition model 272, and acquires an image recognition result. In the following, an example of the image recognition model 272 for site identification will be described, but other trained image recognition models may be used.

The image recognition model 272 is used as a program module that is a part of artificial intelligence software. The image recognition model 272 is a recognizer for which a neural network has been constructed (generated) that inputs an AI correction image and outputs a result of predicting a part of a subject. The neural network is, for example, a CNN (Convolutional Neural Network), which includes an input layer that accepts input of an AI correction image, an output layer that outputs a result of predicting a site of a subject, and an intermediate layer that has been trained by back-propagation.

The input layer has a plurality of neurons that accept the input of the pixel value of each pixel included in the AI correction image, and passes the input pixel value to the intermediate layer. The intermediate layer has a plurality of neurons that extract the image feature amount of the AI correction image, and passes the extracted image feature amount to the output layer. For example, the case where the image recognition model 272 is a CNN will be described as an example. The intermediate layer has a configuration in which a convolution layer for convolving each pixel input from the input layer and a pooling layer for mapping the pixel values convolved in the convolution layer are alternately connected. Therefore, the intermediate layer finally extracts the feature amount of the image while compressing the pixel information of the AI correction image. After that, the intermediate layer predicts the probability that the AI correction image is each part in the subject by the fully-connected layer whose parameters are learned by back-propagation. The prediction result is output to the output layer having a plurality of neurons.

The AI correction image may be input to the input layer after passing through the convolution layer and the pooling layer, which are alternately connected, to extract the feature amount.

The control unit 21 performs learning using a combination of training data including the AI correction image subjected to the second correction process and the label data indicating the type of the part, and generates the image recognition model 272. The control unit 21 inputs the AI correction image to the input layer of the image recognition model 272, performs arithmetic processing in the intermediate layer, and acquires an identification result for identifying the part of the subject from the output layer. The identification result may be a continuous probability value (for example, a value in the range of "0" to "1") corresponding to each part in the subject.

The control unit 21 generates an image for display by superimposing the recognition result output from the trained image recognition model 272 with the endoscopic image based on the captured image subjected to the first correction process and the AI correction image subjected to the second correction process. The control unit 21 outputs the generated display image to the display device 3.

Since the above-mentioned correction processing procedure is the same as the correction process procedure (FIG. 8) described in the first embodiment, the description thereof will be omitted.

According to this embodiment, the accuracy and reproducibility of the feature parameters of the image are improved by performing the geometric distortion correction process on the captured image. Therefore, it is possible to output a highly accurate image recognition result using the trained image recognition model 272.

FIRST MODIFICATION EXAMPLE

The second correction process including the geometric distortion correction and the noise uniformization correction will be described.

The control unit 21 corrects the captured image acquired from the endoscope 1 by the first correction process to generate an endoscopic image. In parallel with the first correction process, the control unit 21 corrects the captured image acquired from the endoscope 1 by the second correction process including geometric distortion correction and noise uniformization correction to generate an AI correction image. The order for executing the process of the geometric distortion correction or the noise uniformization correction is arbitrary, and either correction process may be performed first. Further, instead of the noise uniformization correction process, the noise reduction process may be performed.

The control unit 21 inputs an AI correction image into the trained image recognition model 272, and acquires an image recognition result. Since the subsequent process is the same as the above-mentioned process, the description thereof will be omitted.

In addition to the above-mentioned correction process, any combination and order of correction process may be used. For example, there may be used a combination of the basic correction process and the geometric distortion correction process, a combination of the basic correction process and the noise uniformization correction process, or a combination of the basic correction process and the noise reduction process. Further, the basic correction process may be combined with the geometric distortion correction process and the noise uniformization correction process. Furthermore, a combination of the basic correction process, the geometric distortion correction process, and the noise reduction process may be used. That is, any combination of the basic correction process, the geometric distortion correction process, the noise uniformization correction process, and the noise reduction processing may be used.

According to this modification, it is possible to output a highly accurate image recognition result using the trained image recognition model 272 by performing the second correction process including geometric distortion correction and noise uniformization correction on the captured image.

The embodiments disclosed this time should be considered to be exemplary in all respects without being limited. The scope of the present invention is indicated by the scope of claims, not the above-mentioned meaning, and is intended to include all modifications within the meaning and scope equivalent to the claims.

REFERENCE SIGNS LIST

1 endoscope
11 image sensor
12 treatment tool insertion channel
13 operation unit
14 connector
2 endoscope processor (processor)
21 control unit
22 storage unit
23 operation input unit
24 output unit 25 light source control unit
26 reading unit
27 large-capacity storage unit
271 correction DB
272 image recognition model
72a region candidate extraction unit
72b classification unit
2721 polyp extraction model
2722 ulcer extraction model
28 light source
2a portable storage medium
2b semiconductor memory
2P control program
3 display device
20a image acquisition unit
20b first correction unit
20c second correction unit
20d output unit
20e acquisition unit
20f second acquisition unit
20g acceptance unit

The invention claimed is:

1. An endoscope processor, comprising:
an image acquisition unit that acquires a captured image from an endoscope;
a first correction unit that corrects the captured image acquired by the image acquisition unit;
a second correction unit that corrects the captured image acquired by the image acquisition unit; and
an output unit that outputs an endoscopic image based on the captured image corrected by the first correction unit and a recognition result using a trained image recognition model in which the recognition result is output in a case where the captured image corrected by the second correction unit is input, wherein
the second correction unit performs a noise uniformization correction process, and
the noise uniformization correction process equalizes a standard deviation of noises in a peripheral part and a central part of the captured image.

2. The endoscope processor according to claim 1, wherein the output unit outputs the recognition result superimposed on the endoscopic image.

3. The endoscope processor according to claim 1, wherein the second correction unit performs
correction process on the captured image in the order of a basic correction process, a geometric distortion correction process, or a noise reduction process, or
some of processes selected from the basic correction process, the geometric distortion correction process, the noise uniformization correction process, or the noise reduction process in this order.

4. The endoscope processor according to claim 3, wherein the basic correction process includes an offset correction process, a gain correction process, a shading correction process, or a white balance correction process,
in a case where the gain correction process and the shading correction process are included, the gain correction process is performed before the shading correction process, and
in a case where the gain correction process and the white balance correction process are included, the gain correction process is performed before the white balance correction process.

5. The endoscope processor according to claim 3, wherein
the noise reduction process reduces noises as a whole in the captured image.

6. The endoscope processor according to a claim 3, comprising:
an acquisition unit that acquires a reference rectangular region from which a peripheral portion is removed after the second correction unit corrects the captured image in the geometric distortion correction process,
wherein the output unit outputs the reference rectangular region which is acquired by the acquisition unit.

7. The endoscope processor according to claim 3, comprising:
a second acquisition unit that acquires a reference rectangular region in which pixels are complemented along each side of a corrected captured image after the second correction unit corrects the captured image in the geometric distortion correction process,
wherein the output unit outputs the reference rectangular region which is acquired by the second acquisition unit.

8. The endoscope processor according to claim 1, comprising:
an acceptance unit that accepts a selection of a trained image recognition model to be used from a plurality of the trained image recognition models,
wherein, in a case where the acceptance unit has accepted a selection of the image recognition model, the captured image corrected by the second correction unit is input to the image recognition model which has accepted a selection.

9. An information processing device, comprising:
an image acquisition unit that acquires a captured image from an endoscope;
a first correction unit that corrects the captured image acquired by the image acquisition unit;
a second correction unit that corrects the captured image acquired by the image acquisition unit; and
an output unit that outputs an endoscopic image based on the captured image corrected by the first correction unit and a recognition result using a trained image recognition model in which the recognition result is output in a case where the captured image corrected by the second correction unit is input, wherein
the second correction unit performs a noise uniformization correction process, and
the noise uniformization correction process equalizes a standard deviation of noises in a peripheral part and a central part of the captured image.

10. An endoscope system, comprising:
an endoscope processor; and
an endoscope that is connected to the endoscope processor,
wherein the endoscope processor includes
an image acquisition unit that acquires a captured image from an endoscope, a first correction unit that corrects the captured image acquired by the image acquisition unit, a second correction unit that corrects the captured image acquired by the image acquisition unit, and
an output unit that outputs an endoscopic image based on the captured image corrected by the first correction unit and a recognition result using a trained image recognition model in which the recognition result is output in a case where the captured image corrected by the second correction unit is input, wherein
the second correction unit performs a noise uniformization correction process, and the noise uniformization correction process equalizes a standard deviation of noises in a peripheral part and a central part of the captured image.

\* \* \* \* \*